United States Patent [19]
Rosenberg

[11] Patent Number: 5,678,990
[45] Date of Patent: Oct. 21, 1997

[54] APPARATUS FOR CUSHIONED BITE JUMPING AND THE CORRECTION OF CLASS II MALOCCLUSIONS

[76] Inventor: Farel Rosenberg, 9305 Beverly Crest Dr., Beverly Hills, Calif. 90213

[21] Appl. No.: 634,187

[22] Filed: Apr. 18, 1996

[51] Int. Cl.$^6$ ............................................. A61C 7/36
[52] U.S. Cl. ............................................. 433/19
[58] Field of Search ........................... 433/18, 19, 21

[56] References Cited

U.S. PATENT DOCUMENTS

| | | | |
|---|---|---|---|
| 3,798,773 | 3/1974 | Northcutt | 433/19 |
| 4,382,783 | 5/1983 | Rosenberg | 433/19 |
| 4,462,800 | 7/1984 | Jones | 433/19 |
| 4,472,139 | 9/1984 | Rosenberg | 433/19 |
| 4,708,646 | 11/1987 | Jasper | 433/19 |
| 4,795,342 | 1/1989 | Jones | 433/19 |
| 5,352,116 | 10/1994 | West | 433/19 |
| 5,562,445 | 10/1996 | DeVincenzo et al. | 433/18 |

*Primary Examiner*—Cary E. O'Connor
*Attorney, Agent, or Firm*—Gilbert Kivenson

[57] ABSTRACT

An improved appliance for correcting Class II malocclusions with automatic adjustment as tooth movement, bone movement, or both occur. Instead of employing screw adjustments as does much of the prior art, the present invention applies correcting forces by means of a spring which expands through a pre-set, compressed distance. A linkage is employed to increase corrective forces while maintaining a reasonable closure effort. The appliance can be made in a variety of sizes for incorporation of longer or stronger springs as is required by a particular case. The relative positions of the components of the appliance can be reversed so that it can also serve to correct some Class III protrusions as well.

7 Claims, 6 Drawing Sheets

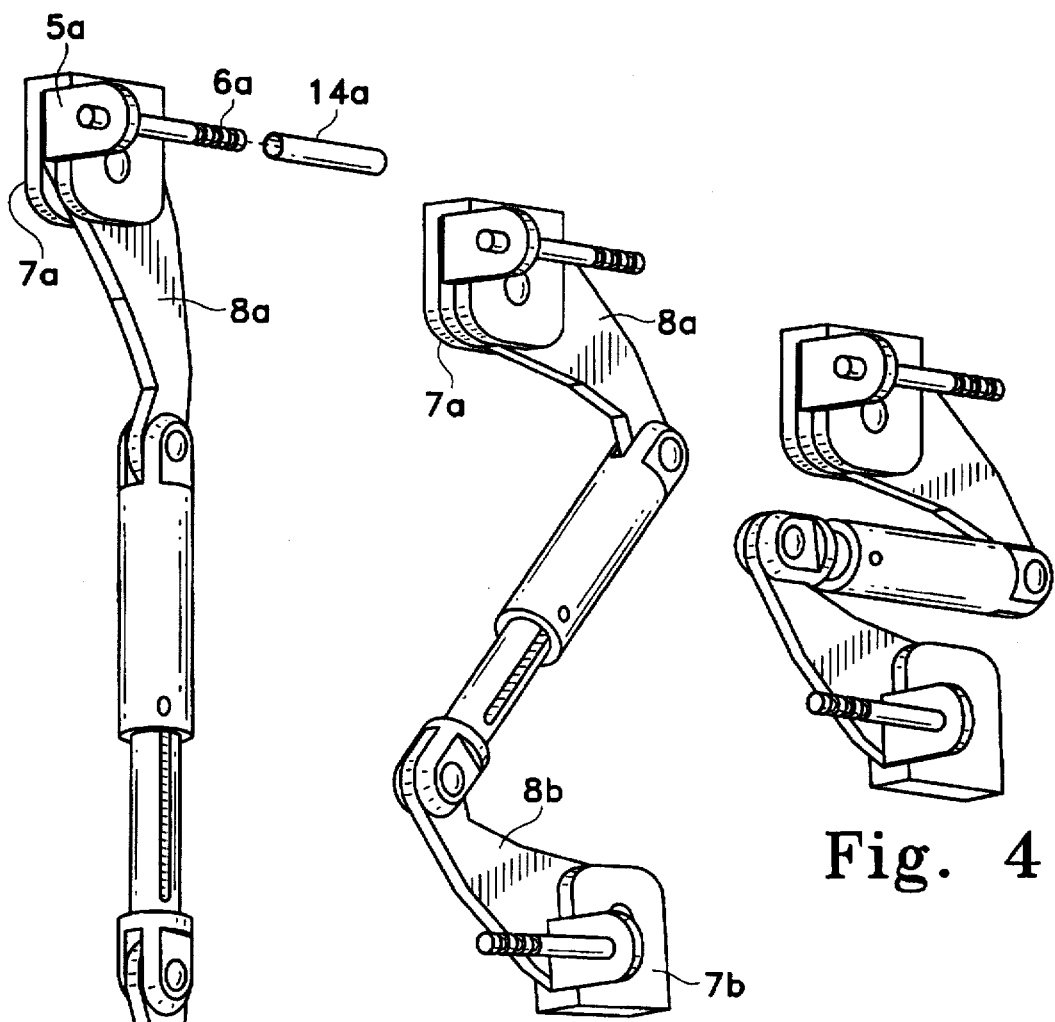
Fig. 4
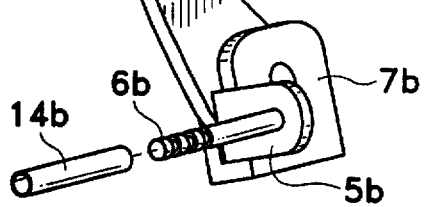
Fig. 2
Fig. 3
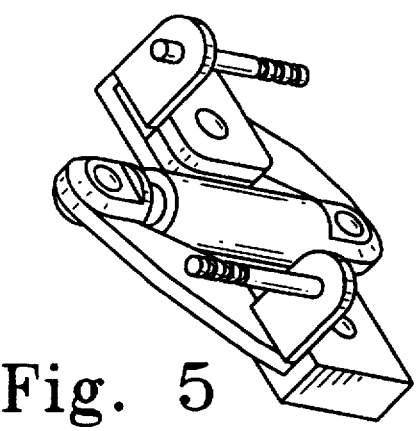
Fig. 5

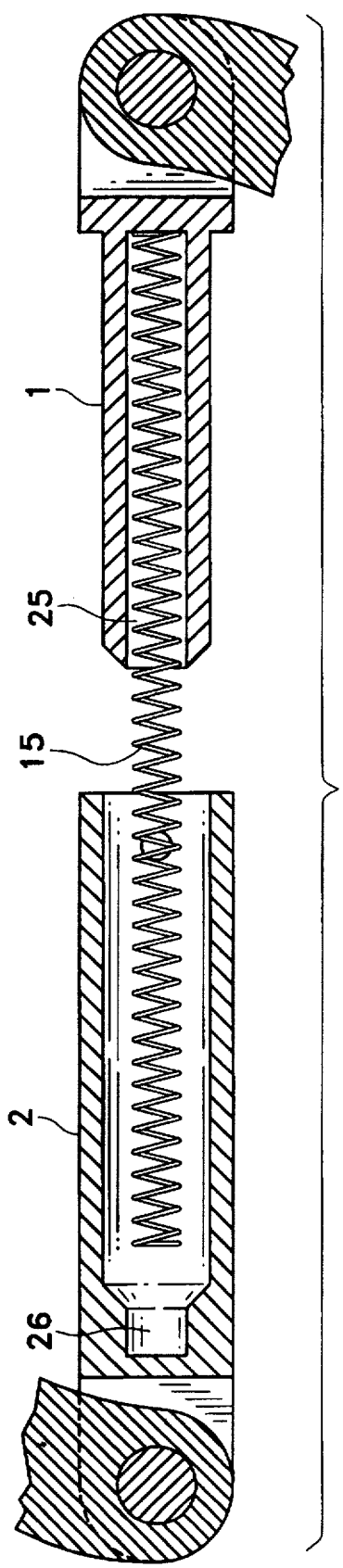
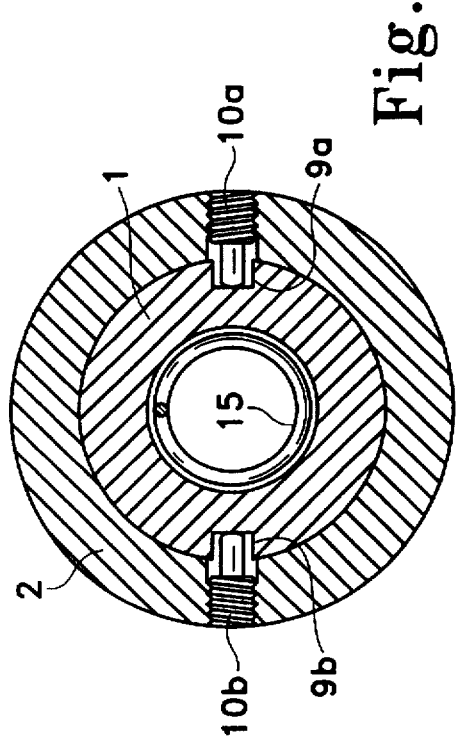
Fig. 7
Fig. 8

APPARATUS FOR CUSHIONED BITE JUMPING AND THE CORRECTION OF CLASS II MALOCCLUSIONS

BACKGROUND OF THE INVENTION

This invention relates to orthopedic and orthodontic appliances for correcting Class II malocclusions in children and adults. In these misorientations, the lower row of teeth occur considerably behind the upper row. This prevents normal alignment of the biting surfaces of the molars in the upper and lower jaws and thus interferes with normal mastication.

The present device is an improvement on the appliance taught in my earlier U.S. Pat. Nos. 4,382,783 and 4,472,139 which employ upper and lower links which are threadably adjustable. The use of screw adjustments connecting the links is undesirable because it introduces weaknesses in a structure which must withstand the considerable pressures generated by the muscles during closing of the mouth.

Another disadvantage of my previous system is the periodic adjustment required as the treatment progresses. The present invention does not use a screw-based adjustment system; it is thus possible to use increased structural ruggedness and to employ an automatically adjustable mechanism.

The present invention is also readily reversible so that it can be used in treating some cases of Class III protrusion where the lower teeth occur forward of the upper row.

SUMMARY OF THE INVENTION

In the present invention, the upper and lower sets of teeth are connected by a piston-cylinder arrangement coupled by pivoted links to housings which, in turn, connect to bands placed on selected teeth in each side of the mouth. When the mouth is closing with the invention in place, the pivoted links act on the piston-cylinder arrangement to redirect part of the closing forces into forward force vectors parallel to the lower jaw.

The invention makes use of a confined spring between the piston and cylinder to transmit forces between upper and lower jaws. If a lighter spring is employed, the invention may be used to bring about tooth movement. With a heavier spring, jaw displacement (as well as tooth movement) may be realized. The invention thus provides both orthodontic and orthopedic functions as well as improved structural ruggedness. The force generated on the jaws by the invention stretches and reorients the muscle structure and, over a period of time, corrects the malocclusion.

The use of linkages permits the invention to be installed on both upper and lower molars in children aged 6 years and up. Prior art devices have required waiting for the growth of lower canine teeth to accommodate these appliances. This limited their use to children 11 years old and older.

If the position of the piston and cylinder and the mounting components is reversed, the appliance will exert backward and downward forces on the lower teeth. This will produce orthodontic pressures during mouth closure which can be used in some cases to treat Class III protrusion. This feature expands the utility of the present appliance beyond the retrusion-correcting capabilities of the prior art.

FIG. 2 is a perspective view of the invention as mounted in the right side of the mouth with the jaws open. The links and piston cylinder arrangement are fully extended.

FIG. 3 is a perspective view of the invention shown in FIG. 2 but with the mouth partially closed.

FIG. 4 is a perspective view of the invention as shown in FIG. 2 but with the mouth completely closed.

FIG. 5 is a perspective view of the invention as shown in FIG. 4 but as it would look with the upper and lower teeth horizontally displaced from one another.

FIG. 7 is a cross-section of the cylinder and piston taken along lines 7-7' of FIG. 6 and disassembled.

FIG. 8 is a cross section of the piston and cylinder showing guide pins and groove and a spring.

Figure 10:
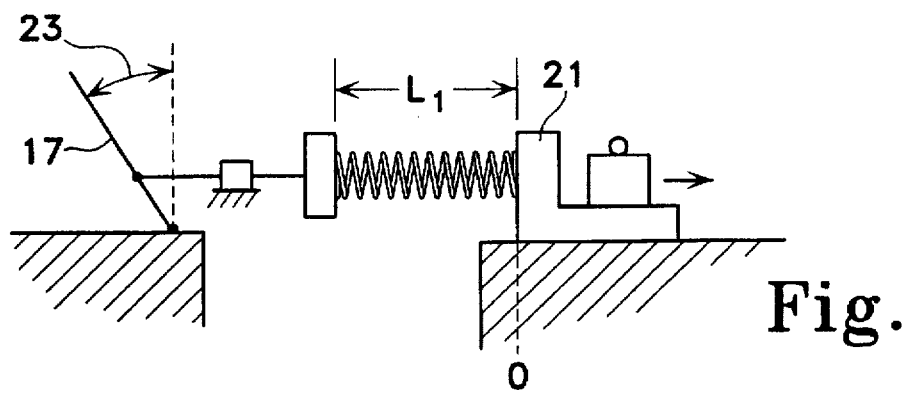
Figure 11:
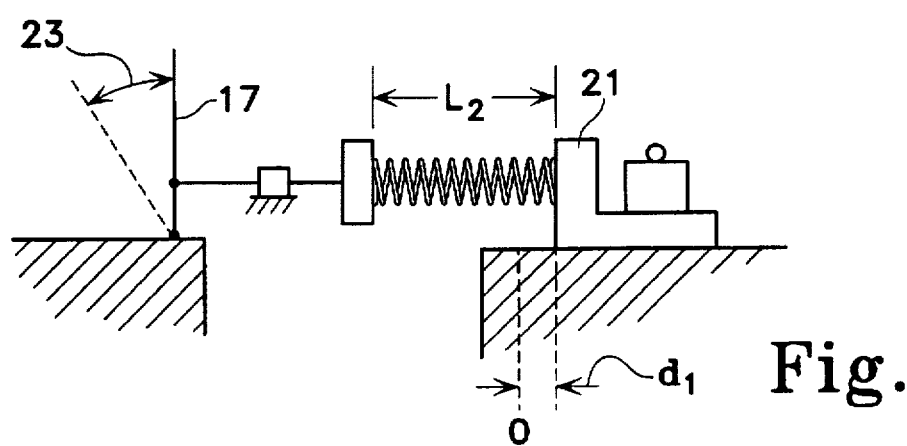
Figure 12:
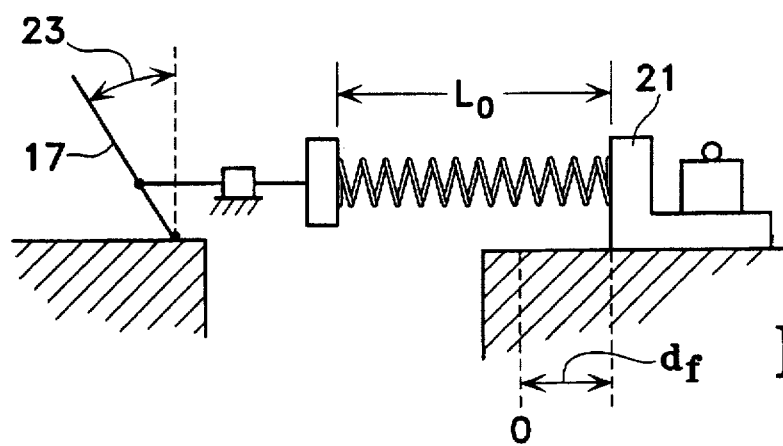

FIGS. 9, 10, 11, and 12 are representational schematics showing the operation of the invention to bring about tooth and jaw displacements. FIG. 12 represents the completion of forward jaw displacement or movement of the lower teeth after the appliance has been in place for some time. FIG. 12 also shows the complete relaxation of the force-transmitting spring at the end of this stage of the treatment.

Figure 1:
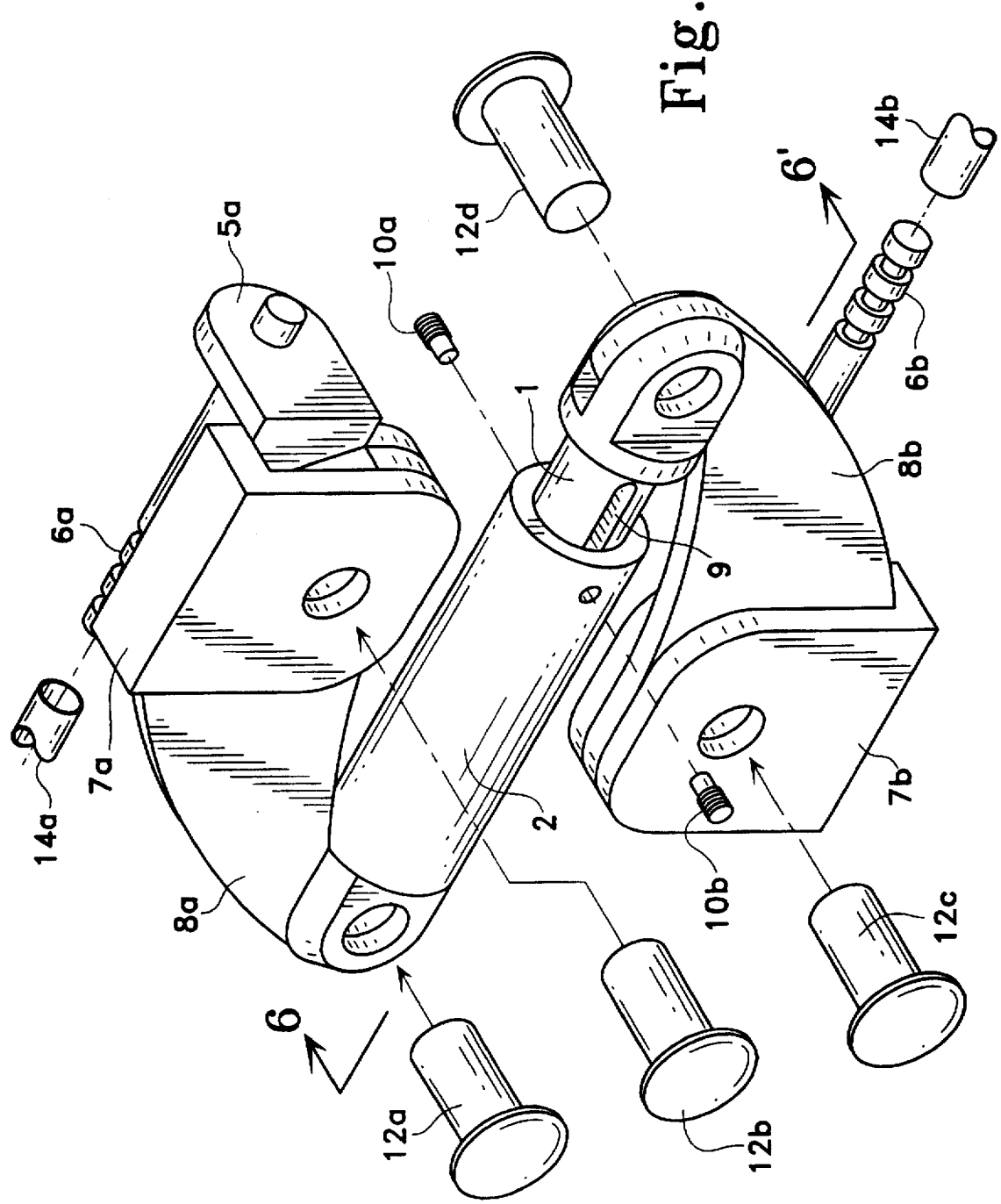
FIG. 1 is a perspective view of the appliance as configured to fit into the right side of the mouth, showing a piston-cylinder arrangement, links, link housings, and mounting spindles.
Figure 13:
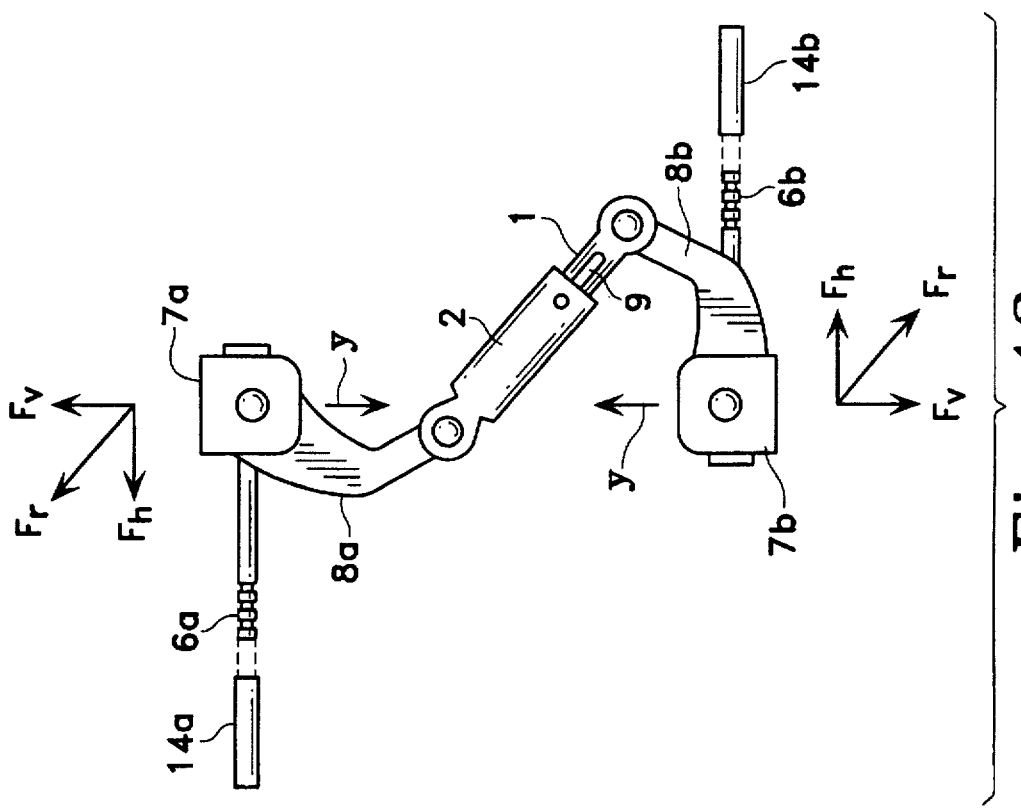

FIG. 13 is a simplified side view of the appliance as shown in FIG. 1 and as designed for use in the right side of the mouth.

Figure 14:
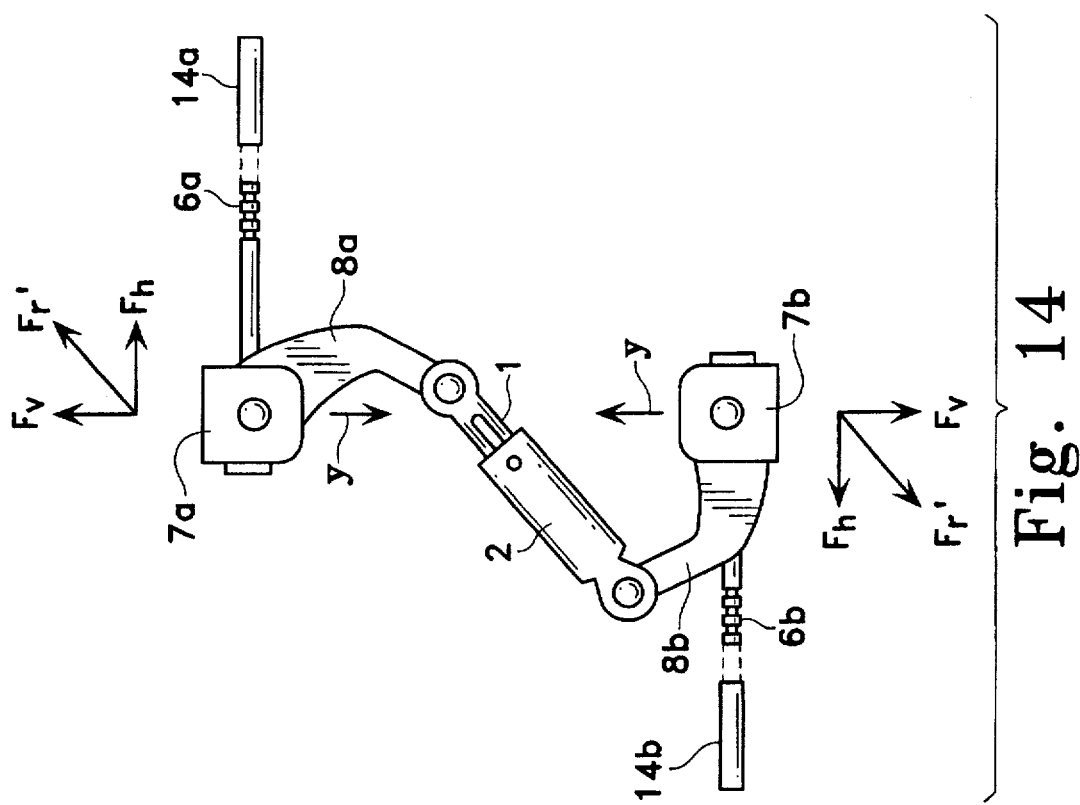

FIG. 14 is a simplified side elevation of the appliance with the cylinder-piston position reversed as are the linkages, linkage housings, and spindle orientations. This provides a downward and backward force on the lower teeth when the mouth is closing.

DESCRIPTION OF THE INVENTION

The invention will first be described with reference to FIGS. 1–8. The use of the force-multiplying links 8a and 8b in FIG. 1 is similar to that taught in my previous patents: U.S. Pat. Nos. 4,382,783 and 4,472,139. The links are coupled to each other in the present invention by a telescoping piston-cylinder 1 and 2. Piston 1 contains a chamber 25 to accommodate spring 15 as shown in FIG. 7. Pins 10a and 10b are held by threads in holes in cylinder 2 (FIGS. 1 and 8) and bear against grooves 9a and 9b cut into the piston 1. This maintains angular alignment of the piston and cylinder as they move linearly with respect to one another and prevents disengagement as the mouth is opened. The end of spring 15 (FIG. 7) engages and is contained in the chamber 26 in cylinder 2 when the appliance is assembled.

The links 8a and 8b are rotatably mounted in their housings 7a and 7b and rotatably joined to the piston and cylinder by the rivets 12a–12d (FIG. 1).

Right- and left-handed versions of the appliance are mounted in the mouth between tubing sections 14a and 14b which have previously been soldered or welded to orthodontic bands. The latter are first cemented to suitable molars as is done in normal orthodontic practice. Spindles 6a and 6b which have been welded into brackets 5a and 5b fit into the tubing sections 14a and 14b and allow transverse movement of the jaws as shown in FIG. 5. Each appliance thus permits opening and closing of the mouth accompanied by link closure and telescoping motion of the piston and cylinder and, in addition, lateral movement of the lower jaw. This is illustrated in FIGS. 2–5. In FIG. 2 is shown the position of the appliance when the mouth is wide open while FIG. 3 shows the appliance with the mouth partially closed. The position of the appliance in FIG. 4 is shown when the mouth is completely closed. FIG. 5 illustrates how the appliance accommodates side-to-side movement of the lower jaw.

Figure 6:
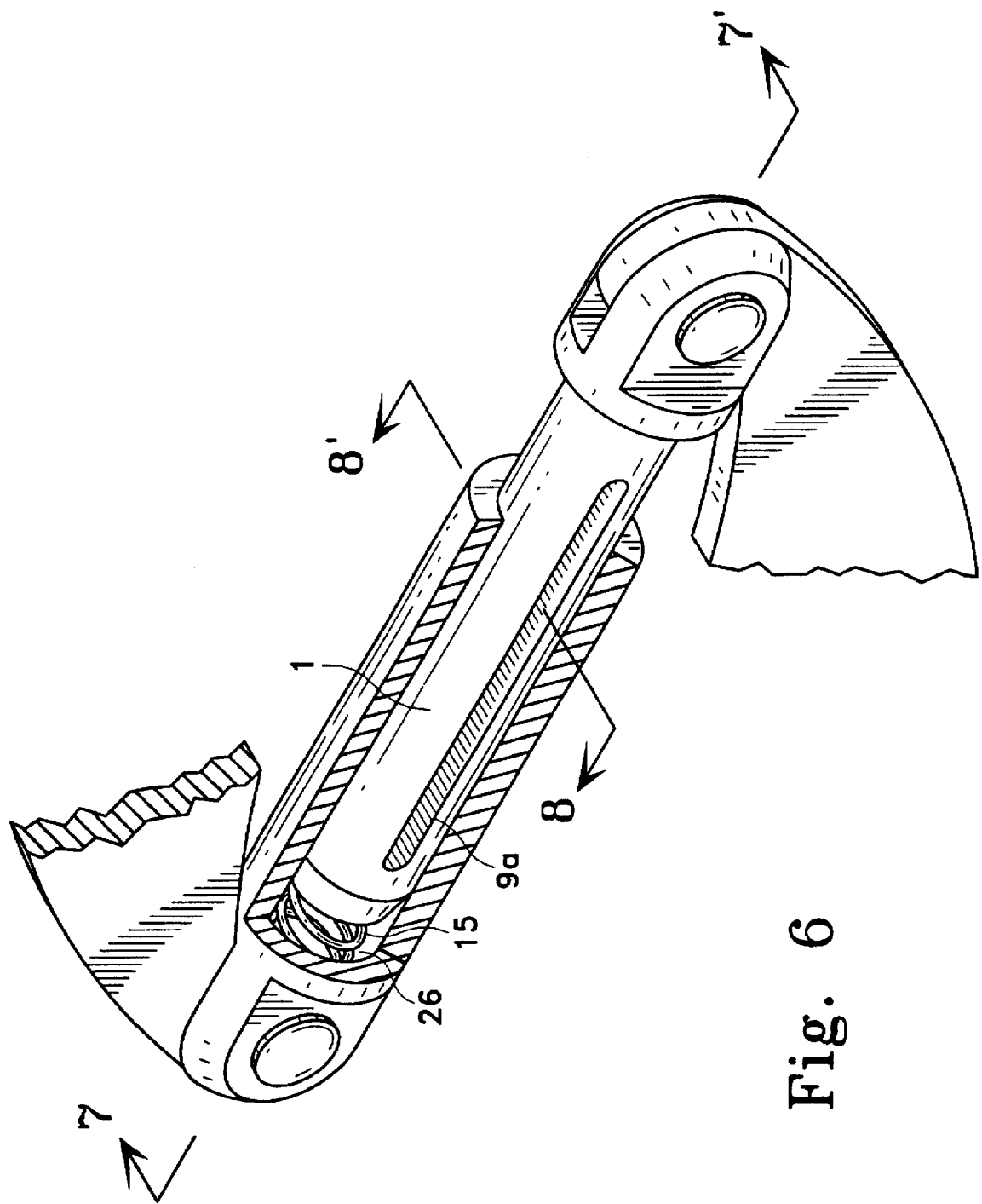
FIG. 6 is an isometric cross-section of the cylinder taken along lines 6-6' of FIG. 1.

As the mouth is closing (FIGS. 2 and 3), links 8a and 8b first turn into the housings 7a and 7b. Further closure of the mouth then compresses spring 15 into chamber 26 (FIG. 6). This causes force to be transmitted between cylinder and piston, resulting in a forward force vector parallel to the lower jaw. This protrudes the latter and produces an occlusion-correcting effect. In this invention, no spacing adjustments between the upper and lower links during treatment need to be made.

The action of spring 15 in producing cushioned motion of the lower jaw and teeth can be explained with reference to FIGS. 9–12 in which levers and a spring represent the coupling between the upper and lower set of teeth.

Figure 9:
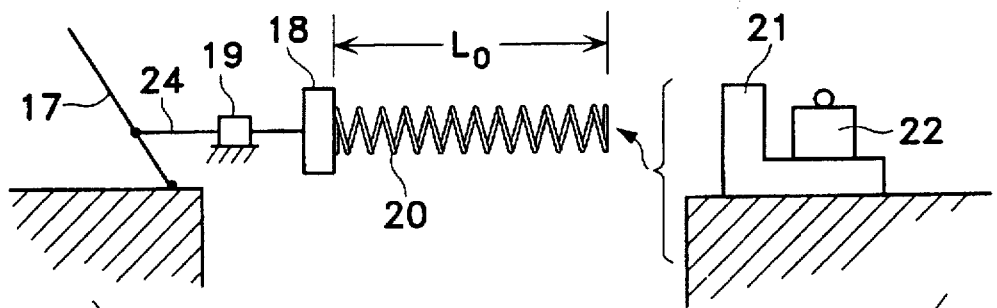

FIG. 9 represents various parts of an appliance before it is installed in the mouth. Lever 17 is pivotably attached to rod 24; the latter is confined to horizontal motion by bearing 19 and terminates in piston 18, to which a length (L0) of compression spring 20 is firmly attached. A lower molar is represented by platform 21 which holds a weight 22. The latter represents the resistance to motion of the lower jaw or teeth. FIG. 10 is a schematic representation of the invention installed in the mouth with spring 20 initially compressed to a new length (L1) (from L0 in the initial installation). Oscillatory movement of lever 17 through arc 23 represents the general opening and closing of the mouth, causing the spring to be compressed to a length less than (L1). The platform 21 is initially at position O (FIG. 10). In time, oscillatory motion of 17 results in the movement of 21 through distance (dl) as shown in FIG. 11. (L2) is greater than (L1) by distance (dl) because of the "permanent" movement of 21. The final result is shown in FIG. 12 where 21 has gone through its maximum movement (df) and spring 20 has returned to its original length (L0). No further movement of 21 occurs when 17 oscillates over the angle 23. The desired advancement of 21 is thus produced without adjustment of the displacement-producing elements during the treatment. The appliance may now be removed from the mouth or the spring replaced by a longer one to continue the correction process.

The preferred embodiment described above is illustrated in simplified form in FIG. 13 showing the piston 1 rotatably attached to the lower link 8b and cylinder 2 rotatably fastened to the upper link 8a. When the mouth is closing in the direction Y—Y, force vectors (Fh) (horizontal and to the right) and (Fv) (vertical and down) are generated with a resultant (Fr) shown. Equal and opposite forces and result are produced in the upper teeth.

A second embodiment of the present invention is illustrated in FIG. 14 where the position of the piston 1 and cylinder 2 have been reversed, as have the permissible rotation directions of links 8a and 8b and the mounting directions of the spindles 6a and 6b. When the mouth now closes in the direction Y—Y, force vectors (Fh) (horizontal again but to the left) and (Fv) (vertical and again down) are generated with a resultant (Fr) (down and to the left) which tends to move the lower teeth backward. This embodiment will be useful in some cases of Class III malocclusions where the lower teeth protrude past the upper row. The upper, resultant force vector (Fr$^1$) is also reversed and has the proper direction for treating this type of malocclusion.

A number of other embodiments of the invention can be made to adapt it for individual cases. Each appliance can, for example, be manufactured with interchangeable piston-cylinder assemblies of various lengths and supplied as a kit. If treatment is started with the shortest piston-cylinder assembly in each of the two appliances and these assemblies are used to the limit of their expansion length without achieving the total correction desired, the appliances may be removed, the next longest piston-cylinder assemblies substituted, and the appliances reinstalled in the patient's mouth. This will allow the treatment to be continued progressively.

Another embodiment of the invention would provide a spring assortment to permit various tooth-moving or jaw-moving pressures to be obtained.

In still another embodiment, the appliances could be constructed with fewer parts for simplicity in manufacture and for use in correcting simpler malocclusions, e.g. the joint between 7a and 8a (FIG. 1) could be non-rotating and fabricated as one piece.

These and other modifications of the invention can be incorporated without departing from the original concepts of the invention.

What is claimed is:

1. Improved dental appliances to orthodontically and orthopedically correct a retrusive dentition, said appliances to be used in the betterment of Class II malocclusions by being installed in each side of the mouth, each appliance comprising:
   (a) upper anchoring means to be installed on a suitable upper tooth acting as a molar;
   (b) lower anchoring means to be installed on a suitable lower tooth acting as a molar;
   (c) an upper link holder rotatably attached to said upper anchoring means;
   (d) a lower link holder rotatably attached to said lower anchoring means;
   (e) an upper link mounted at one end of its ends to permit planar rotation into and out of said upper link holder;
   (f) a lower link mounted at one of its ends so as to permit planar rotation into and out of said lower link holder;
   (g) a cylinder closed at one end and pivotably joined at that end to the free end of said upper link;
   (h) a piston slidably engaged with said cylinder and pivotably joined at its non-engaged end to said lower link;
   (i) an aligning pin mounted through holes in the cylinder and grooves in the sides of the piston so that rotary movement between piston and cylinder is prevented as is pull-out of the piston from the cylinder;
   (j) a compression spring fitting within a chamber in said piston and making contact with a recess in the bottom of said cylinder whereby closing the mouth after the appliances are installed causes the linkages to drive the piston into its cylinder in each side of the mouth, compressing the spring and creating downward and forward forces on the lower jaw and thus, in time, aligning the lower row of teeth with the upper row and achieving a corrected occlusal relationship.

2. Improved dental appliances as described in claim 1 in which said upper and lower anchoring means are comprised of metal bands such as are normally used in orthodontistry and tubing sections welded thereto.

3. Improved dental appliances as described in claim 2 in which each set of upper and lower link holders are welded to spindles which fit into and are free to rotate in the tubing sections.

4. Improved dental appliances as described in claim 1 in each of which a first link is mounted rotatably between the upper link holder and one end of said cylinder, a second link is mounted between the lower link holder and the end of said piston and the piston is inserted in the cylinder with a spring between them so as to be free sliding.

5. Improved dental appliances as described in claim 1 in which the spindles and links permit mouth movement in a side-to-side mode as well as in a masticatory mode with only the masticatory movement creating malocclusion-correcting forces.

6. Improved dental appliances as described in claim 1 in which the piston and cylinder assemblies are rotatably mounted between the upper and lower links whereby closure of the mouth first folds the links into their respective holders, then moves the pistons into their cylinders and finally compresses the springs to create forces in the lower jaw in a downwardly and forwardly direction, said forces being gradually and smoothly applied by virtue of the springs' action.

7. Improved dental appliances as described in claim 1 in which the acting directions of said upper and lower links and said cylinders and pistons can be readily altered to provide reversed forces useful in correcting some Class III malocclusions.

* * * * *